(12) United States Patent
Smith

(10) Patent No.: US 11,535,579 B2
(45) Date of Patent: Dec. 27, 2022

(54) HYDROFLUOROOLEFIN ETHERS, COMPOSITIONS, APPARATUSES AND METHODS FOR USING SAME

(71) Applicant: 3M INNOVATIVE PROPERTIES COMPANY, St. Paul, MN (US)

(72) Inventor: Sean M. Smith, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 250 days.

(21) Appl. No.: 15/733,206

(22) PCT Filed: Dec. 12, 2018

(86) PCT No.: PCT/IB2018/059943
§ 371 (c)(1),
(2) Date: Jun. 10, 2020

(87) PCT Pub. No.: WO2019/116262
PCT Pub. Date: Jun. 20, 2019

(65) Prior Publication Data
US 2021/0101858 A1 Apr. 8, 2021

Related U.S. Application Data

(60) Provisional application No. 62/598,284, filed on Dec. 13, 2017.

(51) Int. Cl.
| | | |
|---|---|---|
| C07C 47/12 | (2006.01) | |
| C07C 43/17 | (2006.01) | |
| C07D 401/12 | (2006.01) | |
| C07D 413/12 | (2006.01) | |
| C09K 5/04 | (2006.01) | |
| C11D 3/24 | (2006.01) | |

(52) U.S. Cl.
CPC ............ *C07C 43/17* (2013.01); *C07D 401/12* (2013.01); *C07D 413/12* (2013.01); *C09K 5/045* (2013.01); *C11D 3/245* (2013.01); *C09K 2205/112* (2013.01); *C09K 2205/22* (2013.01)

(58) Field of Classification Search
CPC .......... H01B 3/24; C11D 7/28; C11D 7/5018; C11D 7/26; C07C 43/12; C07C 43/126; C09K 2205/22; C09K 5/045
See application file for complete search history.

(56) References Cited

U.S. PATENT DOCUMENTS

| | | | |
|---|---|---|---|
| 3,184,533 A | 5/1965 | Eiseman, Jr. | |
| 3,484,470 A * | 12/1969 | Pittman | C08G 77/24 556/448 |
| 3,752,840 A | 8/1973 | Oxenrider | |
| 4,288,651 A | 9/1981 | Wootton | |
| 4,741,744 A | 5/1988 | Wu | |
| 4,782,148 A | 11/1988 | Abe | |
| 4,899,249 A | 2/1990 | Reilly | |
| 4,985,556 A | 1/1991 | Abe | |
| 5,962,390 A | 10/1999 | Flynn | |
| 7,736,537 B1 | 6/2010 | Zastrow | |
| 8,418,530 B1 | 4/2013 | Scaringe | |
| 9,837,801 B2 | 12/2017 | Kieffel | |
| 9,899,125 B2 | 2/2018 | Kieffel | |
| 10,643,764 B2 | 5/2020 | Biquez | |
| 2009/0048424 A1 | 2/2009 | Watakabe | |
| 2011/0076572 A1 | 3/2011 | Amine | |
| 2015/0083979 A1 | 3/2015 | Costello | |
| 2016/0312096 A1 | 10/2016 | Bulinski | |
| 2017/0283365 A1* | 10/2017 | Lamanna | H01M 10/0525 |
| 2017/0349760 A1* | 12/2017 | Friedrich | C09D 4/00 |
| 2018/0040391 A1 | 2/2018 | Kieffel | |
| 2018/0358148 A1 | 12/2018 | Kieffel | |
| 2019/0156968 A1 | 5/2019 | Gautschi | |
| 2021/0317259 A1* | 10/2021 | Friedrich | C07D 303/24 |

FOREIGN PATENT DOCUMENTS

| | | |
|---|---|---|
| EP | 1325949 | 7/2003 |
| GB | 1242180 | 8/1971 |
| GB | 2070012 | 9/1981 |
| JP | S56-25133 | 3/1981 |
| JP | S56-55336 | 5/1981 |
| JP | S64-70445 | 3/1989 |
| JP | H05-325970 | 12/1993 |
| JP | H08-291299 | 11/1996 |
| JP | 2002-187863 | 7/2002 |

(Continued)

OTHER PUBLICATIONS

Abe, "A New Route to Perfluorovinylamines by the Pyrolytic Reaction of an Alkali Metal Salt of Perfluoro (2-dialkylamino-propionic acids)", Chemistry Letters, 1988, vol. 17, No. 11, pp. 1887-1890.

Abe, "An Alternative New Route to Perfluorovinylamines. Pyrolysis of an Alkali Metal Salt of Perfluoro (3-dialkylamino-propionic acids)", Chemistry Letters, 1989, vol. 18, No. 5, pp. 905-908.

Abe, "The Electrochemical Fluorination of Nitrogen-Containing Carboxylic Acids. Fluorination of Dimethylamino-Substituted Carboxylic Acid Derivatives", Journal of Fluorine Chemistry, 1990, vol. 48, pp. 257-279.

Abe, "The Electrochemical Fluorination of Nitrogen-Containing Carboxylic Acids. Fluorination of Methyl Esters of Cyclic Amino-Group Substituted Carboxylic Acids", Journal of Fluorine Chemistry, 1990, vol. 50, pp. 173-196.

(Continued)

*Primary Examiner* — John R Hardee
(74) *Attorney, Agent, or Firm* — Jeffrey M. Olofson

(57) ABSTRACT

A hydrofluoroolefin ether represented by the general Formula (I), compositions that include such compounds, and apparatuses and methods for use that include such compositions and compounds, wherein Formula (I) is represented by: $R_f\text{—O—CH}_2\text{CH=CHCH}_2\text{—O—}R_f$ (I) wherein each Rf group is independently a linear, branched, and/or cyclic perfluoroalkyl group having 2 to 9 carbon atoms and optionally further including 1 to 3 nitrogen and/or oxygen catenary heteroatoms.

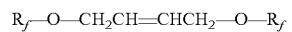

(I)

18 Claims, No Drawings

(56) References Cited

FOREIGN PATENT DOCUMENTS

| WO | WO 1999-037598 | 7/1999 |
|---|---|---|
| WO | WO 2000-015588 | 3/2000 |
| WO | WO 2000-070289 | 11/2000 |
| WO | WO 2002-040102 | 5/2002 |
| WO | WO 2009-141053 | 11/2009 |
| WO | WO 2012-102915 | 8/2012 |
| WO | WO 2013-151741 | 10/2013 |
| WO | WO 2014-037566 | 3/2014 |
| WO | WO 2014-110329 | 7/2014 |
| WO | WO 2015-013155 | 1/2015 |
| WO | WO 2015-040069 | 3/2015 |
| WO | WO 2015-071303 | 5/2015 |
| WO | WO 2015-097143 | 7/2015 |
| WO | WO 2016-048808 | 3/2016 |
| WO | WO 2016-094113 | 6/2016 |
| WO | WO 2016-096129 | 6/2016 |
| WO | WO 2016-109203 | 7/2016 |
| WO | WO 2016-116637 | 7/2016 |
| WO | WO 2016-128571 | 8/2016 |
| WO | WO 2016-198390 | 12/2016 |
| WO | WO 2017-093259 | 6/2017 |
| WO | WO 2017-108141 | 6/2017 |
| WO | WO 2017-114862 | 7/2017 |
| WO | WO 2017-125536 | 7/2017 |
| WO | WO 2017-195070 | 11/2017 |
| WO | WO 2018-039096 | 3/2018 |
| WO | WO 2018-222384 | 12/2018 |
| WO | WO 2018-224908 | 12/2018 |
| WO | WO 2019-082053 | 5/2019 |
| WO | WO 2019-116260 | 6/2019 |
| WO | WO 2019-116264 | 6/2019 |

OTHER PUBLICATIONS

Andersen, "Atmospheric Chemistry of (CF3)2CF-C. ° N: A Replacement Compound for the Most Potent Industrial Greenhouse Gas, SF6", Environmental Science & Technology, 2017, Vo. 51 No. 3, pp. 1321-1329.

Barlow, "Heterocyclic Polyfluoro-Compounds. Part 30. Perfluoroalkylation of trifluoro-1,2,4-triazine", Journal of the Chemical Society, Perkin Transactions 1: Organic and Bio-Organic Chemistry, 1980, pp. 2254-2257.

Barnes, "Photochemistry of halocarbon compounds. Part 4. Photochemical conversions of some fluorinated aza- and Diazacyclohexadienes", Journal of the Chemical Society, Perkin Transactions 1: Organic and Bio-Organic Chemistry, 1981, pp. 3289-3291.

Chambers, "Photochemical conversions of some fluorinated aza- and diazacyclohexadienes", Journal of the Chemical Society, Chemical Communications, 1978, No. 7, pp. 305-306.

Chambers, "Photochemistry of halocarbon compounds. Part 5. Photolysis of fluorinated 1,2,3-triazine derivatives", Journal of the Chemical Society, Perkin Transactions 1: Organic and Bio-Organic Chemistry, 1990, No. 4, pp. 975-981.

Chambers, "Photochemistry of halocarbon compounds. Part 6. Direct Observation of fluorinated azetes", Journal of the Chemical Society, Perkin Transactions 1: Organic and Bio-Organic Chemistry, 1990, No. 4, pp. 983-987.

Chambers, "Possible generation of a fluorinated azacyclobutadiene", Journal of the Chemical Society, Chemical Communications, 1976, No. 24, pp. 1005-1006.

Cheburkov, "Perfluoroalcohols", Journal of Fluorine Chemistry, Dec. 2002, vol. 118, No. 1-2, pp. 123-126.

Chepik, "Electrophilic Alkenylation of Fluoroolefins with Perfluoro(2-alkoxypropenes)", Bulletin of the Academy of Sciences of the USSR, Division of chemical science, Aug. 1991, vol. 40, pp. 1712-1714 (Translated from Izvestiya Akademii Nauk SSSR Seriya Khimicheskaya, No. 8, pp. 1926-1928).

Cherstov, "Sulfotrioxidation of perfluoroisopropyl alkenyl ethers", Bulletin of the Academy of Sciences of the USSR, Division of chemical science, Dec. 1982, vol. 31, pp. 2472-2473 (Translated from Izvestiya Akademii Nauk SSSR Seriya Khimicheskaya, No. 12, pp. 2796-2798).

Ellis, "Cleaning and Contamination of Electronics Components and Assemblies", Electrochemical Publications Limited, 1986, pp. 182-194.

Galimberti, "New catalytic alkylation of in situ generated perfluoroalkyloxy-anions and perfluoro-carbanions", Journal of Fluorine Chemistry, Dec. 2005, vol. 126, No. 11-12, pp. 1578-1586.

Jelier, "A Convenient Route to Tetraalkylammonium Perfluoroalkoxides from Hydrofluoroethers", Angewandte Chemie International Edition, Mar. 2015, vol. 54, No. 10, pp. 2945-2949.

McLinden, "A Thermodynamic Analysis of Refrigerants: Possibilities and Tradeoffs for Low-GWP Refrigerants", International Journal of Refrigeration, Feb. 2014, vol. 38, pp. 80-92.

OECD Test No. 436: "Acute Inhalation Toxicity-Acute Toxic Class Method", OECD Guideline for The Testing of Chemicals, Sep. 2009, 27 pages.

OPPTS 870.1100: "Acute Oral Toxicity" U.S. EPA Health Effects Test Guidelines, Dec. 2002, 37 pages.

Pinnock, "Radiative forcing of climate by hydrochlorofluorocarbons and hydrofluorocarbons", Journal of Geophysical Research: Atmospheres, Nov. 1995, vol. 100, No. D11, pp. 23227-23238.

Wlassics, "Perfluoro Allyl Fluorosulfate (FAFS): A Versatile Building Block for New Fluoroallylic Compounds", Molecules, Dec. 2011, vol. 16, No. 8, pp. 6512-6540.

International Search Report for PCT International Application No. PCT-IB2018-059941, dated Mar. 25, 2019, 5pages.

International Search Report for PCT International Application No. PCT-IB2018-059943, dated Mar. 27, 2019, 5pages.

International Search Report for PCT International Application No. PCT-IB2018-059946, dated Mar. 15, 2019, 4pages.

\* cited by examiner

HYDROFLUOROOLEFIN ETHERS, COMPOSITIONS, APPARATUSES AND METHODS FOR USING SAME

CROSS REFERENCE TO RELATED APPLICATIONS

This application is a national stage filing under 35 U.S.C. 371 of PCT/IB2018/059943, filed Dec. 12, 2018, which claims the benefit of U.S. Provisional Application No. 62/598,284, filed Dec. 13, 2017, the disclosure of which is incorporated by reference in its/their entirety herein.

BACKGROUND

There continues to be a need for inert fluorinated fluids that have low global warming potential while providing high thermal stability, low toxicity, non-flammability, good solvency, and a wide operating temperature range to meet the requirements of various applications. Those applications particularly include, but are not restricted to, heat transfer fluids.

SUMMARY

The present disclosure provides hydrofluoroolefin ethers, compositions including such compounds, apparatuses and methods of using that include such compounds and compositions, which may be used, e.g., in heat transfer fluids and cleaning compositions.

The hydrofluoroolefin ether is represented by the following general formula (I):

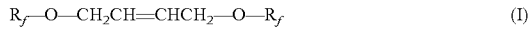

$$R_f\text{—O—}CH_2CH\text{=}CHCH_2\text{—O—}R_f \quad (I)$$

wherein each $R_f$ group is independently a linear, branched, and/or cyclic perfluoroalkyl group having 2 to 9 carbon atoms and optionally further including 1 to 3 nitrogen and/or oxygen catenary heteroatoms. In some embodiments, each $R_f$ group is the same.

In some embodiments, a composition is provided that includes the hydrofluoroolefin ether of Formula (I), which may be in a trans configuration, in a cis configuration, or in a mixture thereof.

In some embodiments, an apparatus for heat transfer is provided that includes: a device; and a mechanism for transferring heat to or from the device, the mechanism including a heat transfer fluid that includes a composition of a hydrofluoroolefin ether of Formula (I).

In some embodiments, a method of transferring heat is provided. The method includes providing a device and transferring heat to or from the device using a heat transfer fluid that includes a composition of a hydrofluoroolefin ether of Formula (I).

Herein, "device" refers to an object or contrivance which is heated, cooled, or maintained at a predetermined temperature.

The term "mechanism" refers to a system of parts or a mechanical appliance including a heat transfer fluid.

The term "alkyl" refers to a monovalent group that is a radical of an alkane, which is a saturated hydrocarbon. The alkyl group can be linear, branched, cyclic, or combinations thereof; "perfluoro-" (for example, in reference to a group or moiety, such as in the case of "perfluoroalkyl") and "perfluorinated" mean a group or compound completely fluorinated such that all hydrogen atoms in the C—H bonds have been replaced by C—F bonds; and a chemical structure that depicts the letter "F" in the center of a ring indicates that all unmarked bonds of the ring are fluorine atoms.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful and is not intended to exclude other claims from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also, herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also, herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the term "room temperature" refers to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

When a group is present more than once in a formula described herein, each group is "independently" selected, whether specifically stated or not. For example, when more than one R group is present in a formula, each R group is independently selected.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION

The present disclosure provides hydrofluoroolefin ethers, compositions including such compounds, apparatuses and methods of using that include such compounds and compositions. In some embodiments, the compositions are used to transfer heat (in heat transfer fluids), and in some embodiments, the compositions are used to clean (in cleaning compositions).

In some embodiments, the present disclosure is directed to a hydrofluoroolefin ether represented by the following general Formula (I):

$$R_f\text{—}O\text{—}CH_2CH\text{=}CHCH_2\text{—}O\text{—}R_f \qquad (I)$$

wherein each $R_f$ group is independently a linear, branched, and/or cyclic perfluoroalkyl group having 2 to 9 carbon atoms and optionally further including 1 to 3 nitrogen and/or oxygen catenary heteroatoms. Such heteroatoms may be included in a N- and/or O-containing 5- or 6-membered perfluorinated ring (preferably a 6-membered perfluorinated ring), which may be a monovalent ring (at the terminus of an alkyl group) or a divalent ring (within the chain of an alkyl group).

In some embodiments of the hydrofluoroolefin ethers of Formula (I), each $R_f$ group is the same.

In some embodiments of the hydrofluoroolefin ethers of Formula (I), each $R_f$ group is independently a linear, branched, and/or cyclic perfluoroalkyl group having 3 to 9 carbon atoms (or having 4 to 9 carbon atoms) and optionally further including 1 to 3 nitrogen and/or oxygen catenary heteroatoms.

In some embodiments of the hydrofluoroolefin ethers of Formula (I), each $R_f$ group is independently a linear or branched perfluoroalkyl group and optionally further including 1 to 3 nitrogen and/or oxygen catenary heteroatoms.

In some embodiments of the hydrofluoroolefin ethers of Formula (I), each $R_f$ group is independently selected from —$(CF_2)_nCF_3$ or —$(CF_2)_nCF(CF_3)_2$, wherein n=1 to 6.

In some embodiments of the hydrofluoroolefin ethers of Formula (I), the N- and/or O-containing perfluorinated ring is selected from the group of:

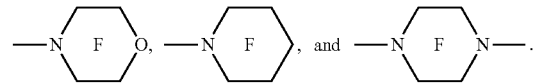

In some embodiments, the hydrofluoroolefin ether of Formula (I) is selected from one of the following:

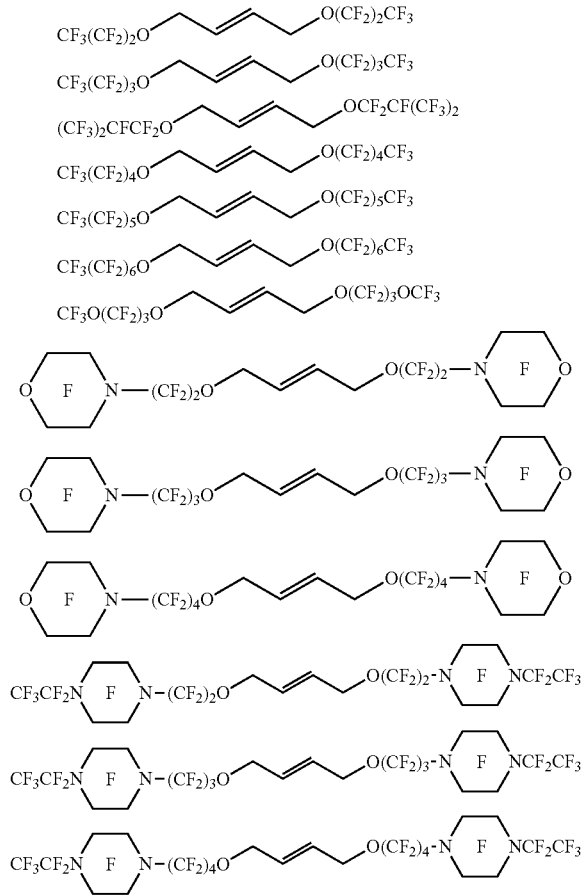

-continued

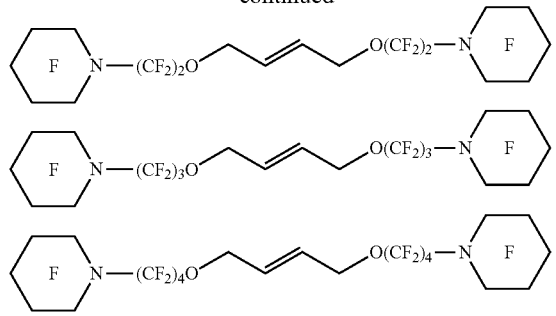

In some embodiments, the hydrofluoroolefin ether of Formula (I) is selected from one of the following:

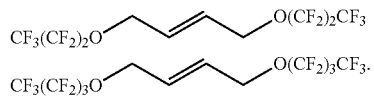

In some embodiments, the hydrofluoroolefin ethers of Formula (I) of the present disclosure may be in a cis configuration or a trans configuration.

In some embodiments, the hydrofluoroolefin ethers of the present disclosure may exhibit properties that render them particularly useful as heat transfer fluids for the electronics industry. For example, the hydrofluoroolefin ethers may be chemically inert (i.e., they do not easily react with base, acid, water, etc.), and may have high boiling points (up to 250° C.), low freezing points (they may be liquid at a temperature lower than −40° C.), low viscosity, high thermal stability, high vapor pressure, good thermal conductivity, adequate solvency in a range of potentially useful solvents, and low toxicity.

The hydrofluoroolefin ethers described herein may also be liquid at room temperature (e.g., 20° C. to 25° C.). In some embodiments, the hydrofluoroolefin ethers have a melting point of lower than −40° C., lower than −50° C., lower than −60° C., lower than −70° C., or lower than −80° C.

The hydrofluoroolefin ethers described herein may be non-flammable. Non-flammability can be assessed by using standard methods such as ASTM D-3278-96 e-1, D56-05 "Standard Test Method for Flash Point of Liquids by Small Scale Closed-Cup Apparatus." In one embodiment, the compound of the present disclosure is non-flammable based on closed-cup flashpoint testing following ASTM D-3278-96 e-1.

Furthermore, in some embodiments, the hydrofluoroolefin ethers of the present disclosure may have a low environmental impact. In this regard, the hydrofluoroolefin ethers may have a global warming potential (GWP) of less than 300, less than 200, less than 100, less than 50, or even less than 20. As used herein, GWP is a relative measure of the warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, r is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the above-described hydrofluoroolefin ethers may be prepared by substitution of a halogenated butene such as, for example, 1,4-dibromobutene, 1-chloro,4-bromobutene, 1,4-dichlorobutene, 1,4-diiodobutene, or the mixture of these butenes, by a tetramethylammonium perfluoroalkoxide. Such tetramethylammonium perfluoroalkoxide may be formed in situ by contacting a hydrofluoroether (HFE) of general formula $R_fOR$ (wherein R is an alkyl group) with trimethylamine. Many polar solvents such as acetonitrile, benzonitrile, N,N-dimethylformamide (DMF), bis(2-methoxyethyl) ether (diglyme), tetraethylene glycol dimethyl ether (tetraglyme), tetrahydrothiophene-1,1-dioxide (sulfolane), N-methyl-2-pyrrolidinone (NM2P), dimethyl sulfone can be used individually or as a mixture.

A composition that includes one or more hydrofluoroolefin ether compounds of Formula (I) may be used for a variety of applications. For example, the hydrofluoroolefin ethers are believed to possess the required stability as well as the necessary short atmospheric lifetime and hence low global warming potential to make them viable environmentally friendly candidates for high temperature heat transfer applications.

In certain embodiments, a mixture of hydrofluoroolefin ether compounds of Formula (I) is provided, at least a portion of which includes linear $R_f$ groups and at least a portion of which includes branched $R_f$ groups.

In certain embodiments, a mixture of hydrofluoroolefin ether compounds of Formula (I) is provided, at least a portion of which are compounds in a cis configuration and at least a portion of which are compounds in a trans configuration.

Minor amounts of optional components can also be added to the compositions to impart particular desired properties for particular uses. Useful components can include conventional additives such as, for example, surfactants, coloring agents, stabilizers, anti-oxidants, flame retardants, and the like, and mixtures thereof.

Heat Transfer Compositions and Methods

Presently, various fluids are used for heat transfer. The suitability of the heat transfer fluid depends upon the application process. For example, in some electronic applications, a heat-transfer fluid that is inert, has a high dielectric strength, low toxicity, good environmental properties, and good heat transfer properties over a wide temperature range is desirable.

In some embodiments, the present disclosure provides an apparatus for heat transfer that includes a device and a mechanism for transferring heat to or from the device. The mechanism for transferring heat may include a heat transfer fluid that includes a composition that includes a hydrofluoroolefin ether of the present disclosure.

In some embodiments, the present disclosure provides a method of transferring heat. The method includes: providing a device; and transferring heat to or from the device using a heat transfer fluid that includes a composition that includes a hydrofluoroolefin ether of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In certain embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibits high dielectric strength, high volume resistivity, and poor solvency for polar materials. Additionally, the heat-transfer fluid should exhibit good mechanical compatibility, that is, it should not affect typical materials of construction in an adverse manner.

The mechanism for transferring heat includes a heat transfer fluid that includes a composition as described herein. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range.

The direction of heat flow (from device or to device) is determined by the relative temperature difference between the device and the heat transfer mechanism.

The heat transfer mechanism may include facilities for managing the heat-transfer fluid, including, but not limited to, pumps, valves, fluid containment systems, pressure control systems, condensers, heat exchangers, heat sources, heat sinks, refrigeration systems, active temperature control systems, and passive temperature control systems.

Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 240° C.

Heat can be transferred by placing the heat transfer mechanism in thermal contact with the device. The heat transfer mechanism, when placed in thermal contact with the device, may remove heat from the device or provide heat to the device, or maintain the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath. In some systems, such as etchers, ashers, PECVD chambers, vapor phase soldering devices, and thermal shock testers, the upper desired operating temperature may be as high as 170° C., as high as 200° C., or even higher.

In vapor phase soldering, heat is transferred from the vapor head-space (e.g., vaporized compound(s) of Formula (I)) to melting solder. Thus, in some embodiments, the apparatus includes a device, such as an electronic component, to be soldered.

Vapor phase soldering is a process application that requires heat transfer fluids that are especially suitable for high temperature exposure. In such application, temperatures of between 170° C. and 250° C. are typically used, with 200° C. being particularly useful, for soldering applications using a lead-based solder and 230° C. useful for the higher melting lead-free solders. Currently, the heat transfer fluids used in vapor phase soldering are of the perfluoropolyether (PFPE) class. While many PFPEs have adequate thermal stability at the temperatures employed, they also possess the notable drawback of being environmentally persistent with extremely long atmospheric lifetimes which, in turn, gives rise to high global warming potentials (GWPs). As such, there is a need for new materials which possess the characteristics of the PFPEs that make them useful in vapor phase soldering as well as in other high temperature heat transfer applications (e.g., chemical inertness, thermal stability and effective heat transfer, liquid over a wide temperature range, good heat-transfer properties over a wide range of temperatures), but which have a much shorter atmospheric lifetime and lower GWPs. It has been discovered that the compounds of the present disclosure can have short atmospheric lifetimes (compared to perfluorinated hydrocarbons and hydrofluorocarbons) while being stable at elevated temperatures, such as the temperatures experienced in vapor phase soldering.

Cleaning Compositions and Methods

In some embodiments, the present disclosure relates to cleaning compositions that include one or more hydrofluoroolefin ethers of Formula (I) of the present disclosure, and one or more co-solvents.

In illustrative embodiments, co-solvents suitable for use in cleaning compositions may include alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.

Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., alpha-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof.

In some embodiments, one or more hydrofluoroolefin ethers of Formula (I) may be present in an amount of at least 50 weight percent (wt-%), at least 60 wt-%, at least 70 wt-%, or at least 80 wt-%, based upon the total weight of the hydrofluoroolefin ether(s) of Formula (I) and the co-solvent(s).

In some embodiments, one or more co-solvents may be present in an amount up to 50 wt-%, up to 40 wt-%, up to 30 wt-%, or up to 20 wt-%, based upon the total weight of the hydrofluoroolefin ether(s) of Formula (I) and the co-solvent(s).

In various embodiments, a cleaning composition may further include one or more surfactants. Suitable surfactants include those surfactants that are sufficiently soluble in the hydrofluoroolefin ethers of Formula (I), and which promote soil removal by dissolving, dispersing, or displacing the soil. One useful class of surfactants are those nonionic surfactants that have a hydrophilic-lipophilic balance (HLB) value of less than 14.

Examples include ethoxylated alcohols, ethoxylated alkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble oil removal.

The surfactant, if used, can be added in an amount sufficient to promote soil removal. In certain embodiments, a surfactant is added in an amount of at least 0.1 wt-%, or at least 0.2 wt-%, based on the weight of the cleaning composition. In certain embodiments, a surfactant is added in an amount of up to 5.0 wt-%, or up to 2.0 wt-%, based on the weight of the cleaning composition.

In some embodiments, the present disclosure relates to a process for cleaning a substrate. The cleaning process can be carried out by contacting a contaminated substrate having one or more contaminants on a surface thereof with a cleaning composition to remove at least a portion of the contaminants. The hydrofluoroolefin ethers of Formula (I) can be utilized alone or in admixture with each other or with other commonly used cleaning solvents as listed above. Such co-solvents can be chosen to modify or enhance the solvency properties of a cleaning composition for a particular use and can be utilized in ratios (of co-solvent to hydrofluoroolefin ethers) such that the resulting composition has no flash point.

If desirable for a particular application, the cleaning composition can further contain one or more dissolved or dispersed gaseous, liquid, or solid additives (for example, carbon dioxide gas, stabilizers, antioxidants, activated carbon, or combinations thereof).

The cleaning processes of the disclosure can also be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics derived therefrom) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

EMBODIMENTS

Embodiment 1 is a hydrofluoroolefin ether represented by the following general formula (I):

$$R_f\text{—O—}CH_2CH\text{=}CHCH_2\text{—O—}R_f \qquad (I)$$

wherein each $R_f$ group is independently a linear, branched, and/or cyclic perfluoroalkyl group having 2 to 9 carbon atoms and optionally further including 1 to 3 nitrogen and/or oxygen catenary heteroatoms.

Embodiment 2 is the hydrofluoroolefin ether of embodiment 1 wherein each $R_f$ group is the same.

Embodiment 3 is the hydrofluoroolefin ether of embodiment 1 or 2 wherein each $R_f$ group is independently a linear, branched, and/or cyclic perfluoroalkyl group having 3 to 9 carbon atoms and optionally further including 1 to 3 nitrogen and/or oxygen catenary heteroatoms.

Embodiment 4 is the hydrofluoroolefin ether of embodiment 3 wherein each $R_f$ group is independently a linear, branched, and/or cyclic perfluoroalkyl group having 4 to 9 carbon atoms and optionally further including 1 to 3 nitrogen and/or oxygen catenary heteroatoms.

Embodiment 5 is the hydrofluoroolefin ether of any one of embodiments 1 to 4 wherein each $R_f$ group is independently a linear, branched, and/or cyclic perfluoroalkyl group having 4 to 9 carbon atoms and further including a N- and/or O-containing 5- or 6-membered (preferably, a 6-membered) perfluorinated ring.

Embodiment 6 is the hydrofluoroolefin ether of embodiment 5 wherein the N- and/or O-containing perfluorinated ring is selected from the group of:

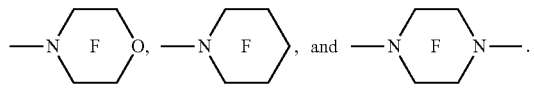

Embodiment 7 is the hydrofluoroolefin ether of any one of embodiments 1 to 4 wherein each $R_f$ group is independently a linear or branched perfluoroalkyl group and optionally further including 1 to 3 nitrogen and/or oxygen catenary heteroatoms.

Embodiment 8 is the hydrofluoroolefin ether of any one of embodiments 1 to 7 which is in a cis configuration or trans configuration.

Embodiment 9 is the hydrofluoroolefin ether of any one of embodiments 1 to 8 wherein each $R_f$ group is independently selected from $—(CF_2)_nCF_3$ or $—(CF_2)_nCF(CF_3)_2$, wherein n=1 to 6.

Embodiment 10 is the hydrofluoroolefin ether of any one of the previous embodiments comprising at least one of the following:

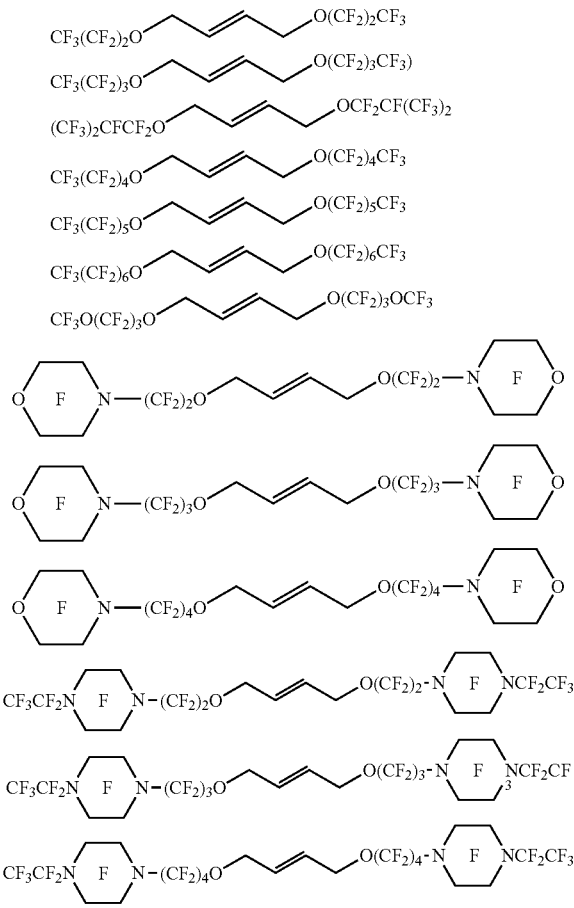

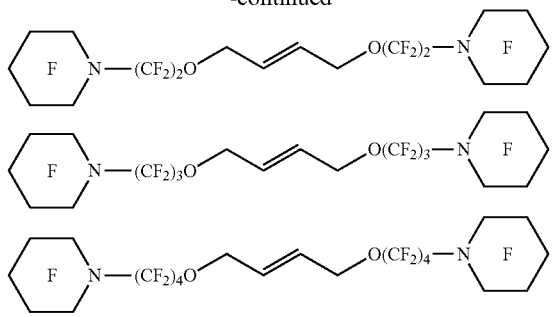

Embodiment 11 is the hydrofluoroolefin ether of embodiment 10 is selected from one of the following:

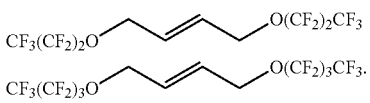

Embodiment 12 is the hydrofluoroolefin ether of any one of the previous embodiments which has a global warming potential (GWP) of less than 300 (less than 200, less than 100, less than 50, or less than 20).

Embodiment 13 is the hydrofluoroolefin ether of any one of the previous embodiments which is non-flammable.

Embodiment 14 is the hydrofluoroolefin ether of any one of the previous embodiments which has a melting point of lower than −40° C. (or lower than −50° C., lower than −60° C., lower than −70° C., or lower than −80° C.).

Embodiment 15 is a composition comprising a hydrofluoroolefin ether compound of any one of the previous embodiments.

Embodiment 16 is the composition of embodiment 15 comprising a mixture of hydrofluoroolefin ether compounds of Formula (I), at least a portion of which includes linear $R_f$ groups and at least a portion of which includes branched $R_f$ groups.

Embodiment 17 is the composition of embodiment 15 or 16 comprising a mixture of hydrofluoroolefin ether compounds of Formula (I), at least a portion of which are in the cis configuration and at least a portion of which are in the trans configuration.

Embodiment 18 is the composition of any one of embodiments 15 to 17 which is a heat transfer fluid.

Embodiment 19 is the composition of embodiment 18 wherein the heat transfer fluid is suitable for vapor phase soldering.

Embodiment 20 is the composition of any one of embodiments 15 to 17 which is a cleaning composition.

Embodiment 21 is the composition of embodiment 20 further comprising one or more co-solvents.

Embodiment 22 is the composition of embodiment 21 wherein the one or more co-solvents are selected from alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, and mixtures thereof.

Embodiment 23 is the composition of embodiment 21 or 22 comprising one or more co-solvents in an amount up to 50 wt-% (or up to 40 wt-%, up to 30 wt-%, or up to 20 wt-%), based upon the total weight of the hydrofluoroolefin ether of Formula (I) and the co-solvent.

Embodiment 24 is the composition of any one of embodiments 20 to 23 further comprising one or more surfactants.

Embodiment 25 is the composition of embodiment 24 wherein the one or more surfactants comprise a nonionic surfactant having a hydrophilic-lipophilic balance (HLB) value of less than 14.

Embodiment 26 is the composition of embodiment 24 or 25 comprising the one or more surfactants in an amount of 0.1 wt-% to 5.0 wt-% (preferably, in an amount of 0.2 wt-% to 2.0 wt-%), based on the weight of the cleaning composition.

Embodiment 27 is the composition of any one of embodiments 20 to 26 further comprising one or more dissolved or dispersed gaseous, liquid, or solid additives selected from carbon dioxide gas, activated carbon, stabilizers, antioxidants, and combinations thereof.

Embodiment 28 is an apparatus for heat transfer comprising: a device; and a mechanism for transferring heat to or from the device, the mechanism comprising a heat transfer fluid of embodiment 18 or 19.

Embodiment 29 is the apparatus of embodiment 28 wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 30 is the apparatus of embodiment 28 or 29 wherein the mechanism for transferring heat is a component in a system for maintaining a temperature or temperature range of an electronic device.

Embodiment 31 is the apparatus of any one of embodiments 28 to 30 wherein the device comprises an electronic component to be soldered.

Embodiment 32 is the apparatus of embodiment 28 wherein the mechanism comprises vapor phase soldering.

Embodiment 33 is a method of transferring heat comprising: providing a device; and transferring heat to or from the device using a heat transfer fluid comprising a composition of any one of embodiments 15 to 19.

Embodiment 34 is the method of embodiment 33 wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 35 is the method of embodiment 33 or 34 wherein transferring heat occurs in a system for maintaining a temperature or temperature range of an electronic device.

Embodiment 36 is the method of embodiment 32 wherein the device comprises an electronic component to be soldered.

Embodiment 37 is the method of embodiment 36 wherein the transferring heat occurs during vapor phase soldering.

Embodiment 38 is a method of cleaning a substrate, the method comprising: providing a contaminated substrate having one or more contaminants on a surface thereof; and contacting the contaminated substrate with a cleaning composition of any one of embodiments 20 to 27 to remove at least a portion of the contaminants.

Embodiment 39 is the method of embodiment 38 wherein the contaminants comprise hydrocarbon contaminants, fluorocarbon contaminants, silicone oils and greases, solder fluxes, particulates, water, and other contaminants encountered in precision, electronic, metal, and medical device cleaning.

Embodiment 40 is the method of embodiment 38 or 39 wherein the cleaning composition is used in the gaseous state, liquid state, or both.

Embodiment 41 is the method of any one of embodiments 38 to 40 wherein the substrate comprises metal, ceramic, glass, polycarbonate, polystyrene, acrylonitrile-butadiene-styrene copolymer, natural fibers and fabrics derived therefrom, synthetic fibers and fabrics derived therefrom, fabrics comprising a blend of natural and synthetic fibers, and composites of the foregoing materials.

EXAMPLES

Objects and advantages of this disclosure are further illustrated by the following examples, but the particular materials and amounts thereof recited in these examples, as well as other conditions and details, should not be construed to unduly limit this disclosure.

Unless otherwise noted, all parts, percentages, ratios, etc. in the examples and the rest of the specification are by weight, and all reagents used in the examples were obtained, or are available, from general chemical suppliers such as, for example, Sigma-Aldrich, Saint Louis, Mo., or may be synthesized by conventional methods. The following abbreviations are used in this section: mL=milliliter, min=minutes, h=hours, g=gram, mg=milligram, mmol=millimole, °C.=degrees Celsius, cSt=centistokes, mmHG=millimeters mercury, kPa=kilopascal.

TABLE 1

| Materials | |
|---|---|
| Material | Description |
| trans-1,4-dibromo-2-butene | Commercially available from Sigma-Aldrich |
| Acetonitrile | $CH_3CN$, commercially available from Sigma-Aldrich |
| DMF | N,N-Dimethylformamide, commercially available from Sigma-Aldrich |
| Tetraglyme | Tetraethylene glycol dimethyl ether, commercially available from Alfa Aesar, Ward Hill, MA, USA |
| Activated carbon | Commercially available from Sigma-Aldrich |
| 4 Angstrom molecular sieves | Commercially available from Sigma-Aldrich |
| $K_2CO_3$ | Potassium carbonate, commercially available from Alfa Aesar |
| Basic alumina | Commercially available from Alfa Aesar |
| Silica gel | Commercially available from Sigma-Aldrich |
| NOVEC 7500 | Engineered fluid, available under the trade designation "3M NOVEC 7500 Engineered Fluid" from 3M Company, Maplewood, MN, USA |

Preparatory Example 1 (PE-1): (E)-1,4-bis(perfluoropropoxy)but-2-ene

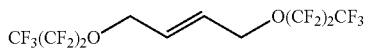

Tetramethylammonium 1,1,2,2,3,3,3-heptafluoropropoxide was prepared as previously described (B. J. Jelier, et al., Angew. Chem. Int. Ed., 54, 2945-2949 (2015)). To a 250 mL round-bottom flask equipped with a magnetic stir bar, water-cooled reflux condenser, temperature probe, and rubber septum were added tetramethylammonium 1,1,2,2,3,3,3-heptafluoropropoxide (74.1 g, 286 mmol) and trans-1,4-dibromo-2-butene (27.2 g, 126 mmol). The flask was then evacuated under reduced pressure and backfilled with $N_2$ gas. Evacuation and back-fill was repeated two more times. To the resultant mixture was then added tetraglyme (250 mL). The reaction mixture was heated to an internal temperature of 80° C. with stirring. After an overnight stir at the same temperature, the resultant reaction mixture was allowed to cool to room temperature followed by the addition of water (200 mL). The bottom, fluorous layer was collected and then analyzed by GC-FID which indicated an uncorrected purity of 72% 1,4-bis(1,1,2,2,3,3,3-heptafluoropropoxy)but-2-ene. The crude mixture was then purified by concentric tube distillation (71° C./3.1 mmHg (0.41 kPa)) affording the title compound (35 g, 65% yield) as a colorless oil. GC-MS analysis confirmed formation of the title compound, 1,4-bis(1,1,2,2,3,3,3-heptafluoropropoxy)but-2-ene.

Preparatory Example 2 (PE-2): (E)-1,4-bis(perfluorobutoxy)but-e-ene

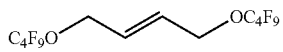

A mixture of tetramethylammonium 1,1,2,2,3,3,4,4,4-nonafluorobutoxide and tetramethylammonium 1,1,2,3,3,3-hexafluoro-2-trifluoromethylpropoxide was prepared as previously described (B. J. Jelier, et al., Angew. Chem. Int. Ed., 54, 2945-2949 (2015)). To a 250 mL three-neck round bottom flask equipped with a temperature probe, magnetic stir bar, and water-cooled reflux condenser were added a mixture of tetramethylammonium 1,1,2,2,3,3,3-heptafluoropropoxide (35.1 g, 113 mmol) and tetramethylammonium 1,1,2,3,3,3-hexafluoro-2-trifluoromethylpropoxide and 1,4-dibromo-2-butene (10.9 g, 50.9 mmol). The flask was then evacuated under reduced pressure and backfilled with $N_2$ gas. Evacuation and back-fill was repeated two more times. To the resultant mixture was then added acetonitrile (35 mL). The resultant mixture was heated to a heating mantle temperature of 80° C. followed by an overnight stir. The resultant reaction mixture was allowed to cool to room temperature followed by the addition of water (200 mL). The bottom, fluorous layer was collected and then analyzed by GC-FID which indicated an uncorrected purity of 85% 1,4-bis(perfluorobutoxy)but-2-ene. GC-MS analysis of the crude product confirmed formation of the title compound, 1,4-bis(perfluorobutoxy)but-2-ene.

Example 1 (EX-1

Vapor Pressure of PE-1 was measured using the stirred-flask ebulliometer method described in ASTM E-1719-97 "Vapor Pressure Measurement by Ebulliometry." This method is also referred to as "Dynamic Reflux." The method used a 50 mL glass round-bottom flask. Vacuum was measured and controlled using a vacuum controller available from J-KEM Scientific, Inc., St. Louis, Mo., USA. The pressure transducer was calibrated on the day of measurement by comparison with full vacuum and with an electronic barometer. The procedure began by slowly heating the material, then applying vacuum until boiling occurred and a steady dropwise reflux rate was established. Pot temperature and pressure were recorded, then the vacuum controller was set for a higher absolute pressure and the material was heated further until a new reflux point was established. The pressure level was raised in increments. Results are presented in Table 2. The results summarized in Table 2 indicate a wide liquid operating temperature range, which renders these materials useful in heat transfer and vapor phase soldering applications.

TABLE 2

Vapor Pressure Results

| Temp (° C.) | Vapor Pressure in mmHg (kPa) |
|---|---|
| 41.4 | 2.5 (0.33) |
| 73.2 | 16.5 (2.20) |
| 109.6 | 96.7 (12.9) |
| 128.3 | 195.7 (26.09) |
| 149.0 | 393.7 (52.49) |
| 170.6 | 743.1 (99.07) |
| 170.8 | 760 (101) |

Example 2 (EX-2

Kinematic viscosity of PE-1 was measured using a Viscosity Timer available under the trade designation "AVS 350" from SI Analytics, College Station, Tex., USA. For temperatures below 0° C., a temperature control bath available from Lawler Manufacturing Corporation, Edison, N.J., USA was used. The viscometer measurements stand and glass viscometer were immersed in a temperature-controlled liquid bath filled with NOVEC 7500. The Lawler temperature bath was fitted with a copper tubing coil for liquid nitrogen cooling with fine temperature control provided by the bath's electronic temperature control heater. The fluid was mechanically stirred to provide uniform temperature in the bath. The bath controls temperature within 0.1° C., measured by the built-in RTD temperature sensor. The sample liquid was added to the viscometer between the two fill lines etched on the viscometer. The AVS 350 automatically pumped the sample fluid above the upper timing mark then released the fluid followed by measurement of efflux times between the upper and lower timing marks. The fluid meniscus was detected by optical sensors as it passed each timing mark. The sample was drawn up and measured repeatedly, averaging multiple measurements.

The glass viscometers were calibrated using certified kinematic viscosity standard fluids available from Cannon Instrument Company, State College, Pa., USA to obtain a calibration constant (centistokes per second) for each viscometer.

The measured kinematic viscosity (centistokes) which is the average efflux time (seconds)×constant (centistokes/ second) is presented in Table 3. The data summarized in Table 3 indicates a favorable low temperature liquid range, which renders these materials useful in heat transfer applications.

TABLE 3

Kinematic Viscosity Measurement Results

| Temp (° C.) | Kinematic Viscosity (cSt) |
|---|---|
| 0.0 | 3.16 |
| −10.0 | 4.28 |
| −30.0 | 10.24 |
| −40.0 | 17.44 |
| −50.0 | 28.23 |
| −60.0 | 59.59 |

Example 3 (EX-3

Melting point of PE-1 was measured on a differential scanning calorimeter available under the trade designation "Q2000 DSC" from TA Instruments, New Castle, Del., USA. The melting point was measured to be in the range of −78° C. to −90° C. using the following temperature program: equilibrate at −90.00° C., ramp 10.00° C./min to 25.00° C., ramp 10.00° C./min to −90.00° C., ramp 10.00° C./min to 25.00° C.

Example 4 (EX-4

Thermal stability of PE-1 was measured by charging 1.0 g of PE-1 into each of seven glass vials and adding 100 mg absorbent as indicated in Table 4, below. The samples were stirred for 24 h at the temperatures indicated in Table 4 and then analyzed for purity by GC-FID. The data summarized in Table 4 indicates that the material would be useful for heat transfer applications given its chemical and thermal stability in the presence of various acidic and basic additives.

TABLE 4

Thermal Stability Results

| | No Adsorbent | No Adsorbent | Activated Carbon | 4 Angstrom Molecular Sieves | $K_2CO_3$ | Basic Alumina | Silica Gel |
|---|---|---|---|---|---|---|---|
| Temp. (°C.) | 25 | 60 | 60 | 60 | 60 | 60 | 60 |
| Purity (%) | 91.7 | 91.7 | 91.8 | 91.9 | 91.6 | 92.0 | 91.7 |

The complete disclosures of the patents, patent documents, and publications cited herein are incorporated by reference in their entirety as if each were individually incorporated. To the extent that there is any conflict or discrepancy between this specification as written and the disclosure in any document that is incorporated by reference herein, this specification as written will control. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A hydrofluoroolefin ether represented by the following general formula (I):

$$R_f\text{—O—CH}_2\text{CH}\!=\!\text{CHCH}_2\text{—O—}R_f \quad \text{(I)}$$

wherein each $R_f$ group is independently a linear, branched, and/or cyclic perfluoroalkyl group having 2 to 9 carbon atoms and wherein each $R_f$ group contains a —$CF_2$-group adjacent to the oxygen atom.

2. The hydrofluoroolefin ether of claim 1 wherein each $R_f$ group is the same.

3. The hydrofluoroolefin ether of claim 1 wherein each $R_f$ group is independently a linear, branched, and/or cyclic perfluoroalkyl group having 3 to 9 carbon atoms and optionally further including 1 to 3 nitrogen and/or oxygen catenary heteroatoms.

4. The hydrofluoroolefin ether of claim 3 wherein each $R_f$ group is independently a linear, branched, and/or cyclic perfluoroalkyl group having 4 to 9 carbon atoms and optionally further including 1 to 3 nitrogen and/or oxygen catenary heteroatoms.

5. The hydrofluoroolefin ether of claim 1 wherein each $R_f$ group is independently a linear or branched perfluoroalkyl group and optionally further including 1 to 3 nitrogen and/or oxygen catenary heteroatoms.

6. The hydrofluoroolefin ether of claim 1 which is in a cis configuration or a trans configuration.

7. The hydrofluoroolefin ether of claim 1 wherein each $R_f$ group is independently selected from —$(CF_2)_n CF_3$ or —$(CF_2)_n CF(CF_3)_2$, wherein n=1 to 6.

8. The hydrofluoroolefin ether of claim 1, wherein the hydrofluoroolefin is selected from at least one of the following:

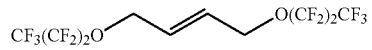

-continued

-continued

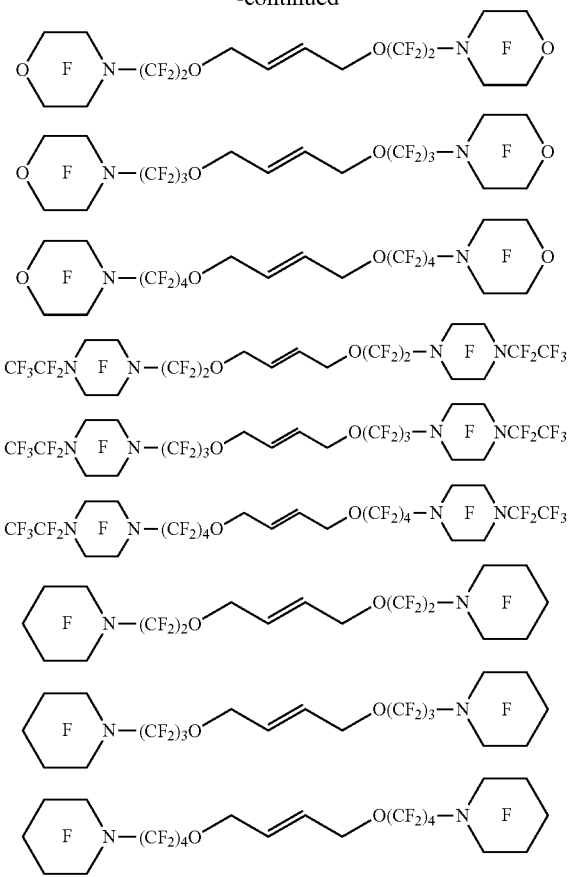

9. The hydrofluoroolefin ether of claim 1, wherein the hydrofluoroolefin ether has a global warming potential (GWP) of less than 300.

10. The hydrofluoroolefin ether of claim 1, wherein the hydrofluoroolefin ether is non-flammable.

11. A composition comprising the hydrofluoroolefin ether compound of claim 1.

12. The composition of claim 11 comprising a mixture of hydrofluoroolefin ether compounds of Formula (I), at least a portion of which includes linear $R_f$ groups and at least a portion of which includes branched $R_f$ groups.

13. The composition of claim 11 comprising a mixture of hydrofluoroolefin ether compounds of Formula (I), at least a portion of which are in the cis configuration and at least a portion of which are in the trans configuration.

14. The composition of claim 11 which is a heat transfer fluid.

15. The composition of claim 11 which is a cleaning composition.

16. An apparatus for heat transfer comprising:
a device; and
a mechanism for transferring heat to or from the device, the mechanism comprising a heat transfer fluid comprising a composition of claim 14.

17. A method of transferring heat comprising:
providing a device; and
transferring heat to or from the device using a heat transfer fluid comprising a composition of claim 14.

18. A method of cleaning a substrate, the method comprising:
providing substrate having one or more contaminants on a surface thereof; and
contacting the contaminated substrate with a cleaning composition of claim 17 to remove at least a portion of the contaminants.

* * * * *

UNITED STATES PATENT AND TRADEMARK OFFICE
CERTIFICATE OF CORRECTION

PATENT NO. : 11,535,579 B2
APPLICATION NO. : 15/733206
DATED : December 27, 2022
INVENTOR(S) : Smith Page 1 of 1

It is certified that error appears in the above-identified patent and that said Letters Patent is hereby corrected as shown below:

In the Claims

Column 18

Line 55, In Claim 8, delete "  " and insert --  --, therefor.

Column 20
Line 33, In Claim 18, delete "claim 17" and insert -- claim 15 --, therefor.

Signed and Sealed this
Third Day of December, 2024

*Katherine Kelly Vidal*

Katherine Kelly Vidal
*Director of the United States Patent and Trademark Office*